United States Patent [19]
Ollar

[11] Patent Number: 5,846,760
[45] Date of Patent: Dec. 8, 1998

[54] METHOD FOR DETERMINING A PRESENCE OR ABSENCE OF A NONPARAFFINOPHILIC HYDROPHOBIC MICROORGANISM IN A BODY SPECIMEN AND AN ASSOCIATED KIT

[75] Inventor: Robert-A. Ollar, Milford, Pa.

[73] Assignee: Infectech, Inc., Sharon, Pa.

[21] Appl. No.: 969,587

[22] Filed: Nov. 13, 1997

[51] Int. Cl.[6] ............................... C12Q 1/02; C12Q 1/04; C12Q 1/24; C12Q 1/00
[52] U.S. Cl. ................................... 435/29; 435/34; 435/4; 435/30; 435/36; 435/42; 435/975; 436/63
[58] Field of Search .................................. 435/29, 34, 4, 435/30, 36, 42, 975; 436/63

[56] References Cited

U.S. PATENT DOCUMENTS

| | | | |
|---|---|---|---|
| 5,153,119 | 10/1992 | Ollar | 435/34 |
| 5,316,918 | 5/1994 | Ollar | 435/34 |
| 5,472,877 | 12/1995 | Ollar | 435/288.1 |
| 5,569,592 | 10/1996 | Ollar | 435/32 |
| 5,637,501 | 6/1997 | Ollar et al. | 435/286.2 |
| 5,639,675 | 6/1997 | Felder et al. | 435/29 |
| 5,641,645 | 6/1997 | Felder et al. | 435/32 |
| 5,654,194 | 8/1997 | Felder et al. | 435/287.9 |
| 5,663,056 | 9/1997 | Ollar et al. | 435/29 |
| 5,668,010 | 9/1997 | Felder et al. | 435/287.9 |
| 5,677,169 | 10/1997 | Ollar et al. | 435/287.9 |

*Primary Examiner*—Louise N. Leary
*Attorney, Agent, or Firm*—David V. Radack; Eckert Seamans Cherin & Mellott, LLC

[57] ABSTRACT

The method of the invention involves providing a first receptacle and a second receptacle. The first receptacle contains a sterile aqueous broth and the second receptacle contains an aqueous broth including a carbon source. The method then includes placing into the first receptacle a first support surface having a paraffin wax coating thereon and placing into the second receptacle a second support surface having a hydrophobic material coating thereon. A body specimen, such as sputum, is then introduced into each of the first and second receptacles. The presence of a nonparaffinophilic hydrophobic microorganism in the body specimen is determined by observing (i) a lack of microorganism growth on the paraffin coated material of the first support surface and (ii) a presence of microorganism growth on the hydrophobic material coating of the second support surface.

An associated kit is also disclosed.

15 Claims, 2 Drawing Sheets

METHOD FOR DETERMINING A PRESENCE OR ABSENCE OF A NONPARAFFINOPHILIC HYDROPHOBIC MICROORGANISM IN A BODY SPECIMEN AND AN ASSOCIATED KIT

BACKGROUND OF THE INVENTION

This invention relates to a method for determining a presence or absence of a nonparaffinophilic hydrophobic microorganism in a body specimen and an associated kit.

Several of my United States Patents disclose a method of identifying paraffinophilic and nonparaffinophilic microorganisms in a body specimen. Focussing particularly on detection of paraffinophilic microorganisms, a paraffin slide is placed into a receptacle containing a sterile aqueous broth. After this, a body specimen, such as fecal matter, is introduced into the receptacle. As the broth contains no carbon source for food for the microorganism, if the microorganism is a paraffinophilic microorganism, it will be baited by and attach to the paraffin coating on the slide in order to utilize the paraffin wax as a food/carbon source. By observing the microorganism growth on the slide, and by (if desired) performing a sequence of assays, the paraffinophilic microorganisms can be identified.

This method, however, does not eliminate the potential presence of a nonparaffinophilic hydrophobic microorganism, such as *M. tuberculosis*. Thus, what is needed is a simple, inexpensive and easy to use method and kit that will allow the determination of the presence or absence of a nonparaffinophilic hydrophobic microorganism.

SUMMARY OF THE INVENTION

The method and kit of the invention have met or exceeded the above-mentioned needs as well as others. The method of the invention involves providing a first receptacle and a second receptacle. The first receptacle contains a sterile aqueous broth and the second receptacle contains an aqueous broth including a carbon source. The method then includes placing into the first receptacle a first support surface having a paraffin wax coating thereon and placing into the second receptacle a second support surface having a hydrophobic material coating thereon. A body specimen, such as sputum, is then introduced into each of the first and second receptacles. The presence of a nonparaffinophilic hydrophobic microorganism in the body specimen is determined by observing (i) a lack of microorganism growth on the paraffin coated material of the first support surface and (ii) a presence of microorganism growth on the hydrophobic material coating of the second support surface.

An associated kit is also provided which consists of a first receptacle, a second receptacle, a first support surface having a paraffin wax coating thereon and a second support surface having a hydrophobic material coating thereon. Optionally, a first container having a sterile aqueous broth therein and a second container having an aqueous broth including a carbon source therein can also be provided.

BRIEF DESCRIPTION OF THE DRAWINGS

A full understanding of the invention can be gained from the following detailed description of the invention when read in conjunction with the accompanying drawings in which.

DETAILED DESCRIPTION

As used herein, the term "paraffinophilic microorganism" means a microorganism that can employ paraffin as a source of carbon in a basal salt media, devoid of other forms of carbon. The organism may be bacterial or fungal in nature. The term shall expressly include, but not be limited to, the following microorganisms: Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liquefaciens; Ahnl, Pem. Fluorescens Denitrificans; Pseudomonas Aeruginosa; Streptomyces Spp.; and Mycobacterium Marinum.

As used herein, the term "nonparaffinophilic microorganism" means any microorganism sustained by a carbon source other than paraffin.

As used herein, the term "nonparaffinophilic hydrophobic microorganism" means a nonparaffinophilic microorganism that, when inoculated into an aqueous broth containing a dissolved carbon source, will prefer to grow upon a hydrophobic surface introduced into the broth as opposed to growing within the aqueous broth itself. Examples of such nonparaffinophilic hydrophobic microorganisms include, but are not limited to, the following: *M. tuberculosis* complex (*M. tuberculosis, M. bovis, M. africanum, M. microti*); *M. paratuberculosis; M. leprae; pseudomonads;* and nocardial species.

As used herein, the term "patient" refers to a member of the animal kingdom, including human beings.

Figure 1:
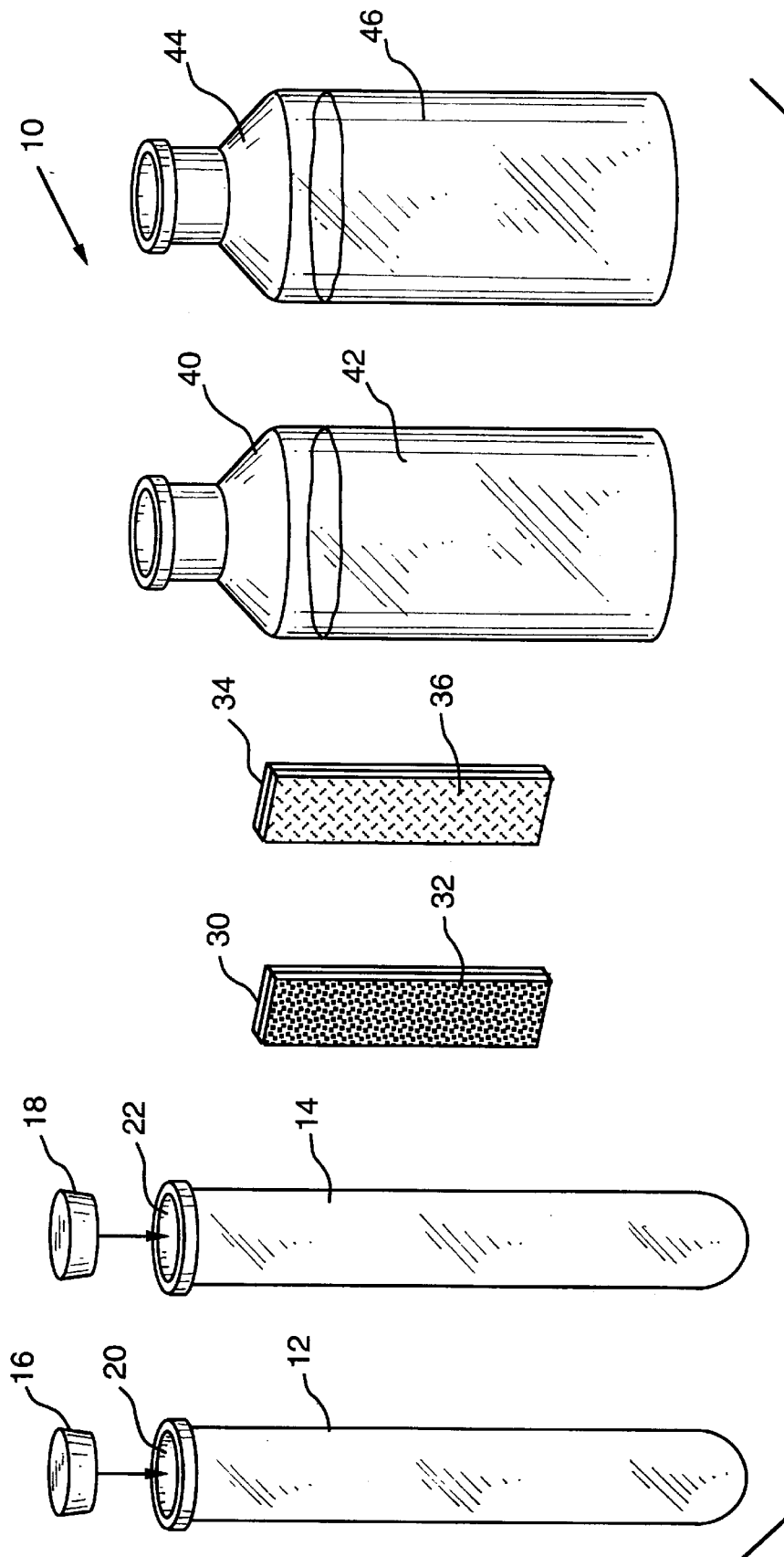
FIG. 1 is a perspective view of the various components of the kit of the invention.

Referring now to FIG. 1, the kit 10, in its disassembled form, is shown. The kit 10 consists of a first receptacle, such as a first glass test tube 12, and a second receptacle, such as a second glass test tube 14, each having respective stoppers 16, 18 (either plastic friction fit or plastic screw cap type) enclosing the respective openings 20, 22 of the test tubes 12 and 14. The kit 10 further consists of a first support surface, such as a first glass slide 30, having thereon a paraffin wax coating 32, and a second support surface, such as a second glass slide 34, having thereon a hydrophobic material coating 36 (discussed in more detail below). The kit 10 optionally can also include a first container 40 containing a sterile aqueous broth, such as Czapek broth 42, and a second container 44 containing an aqueous broth including a carbon source, the carbon being dissolved in the broth. One type of aqueous broth including a dissolved carbon source is Middlebrook 7H9 broth 46. The kit 10 can be packaged in an attractive container, such as a box (not shown), to make it suitable for sales to medical facilities, such as hospitals, laboratories or doctor's offices.

Figure 2:
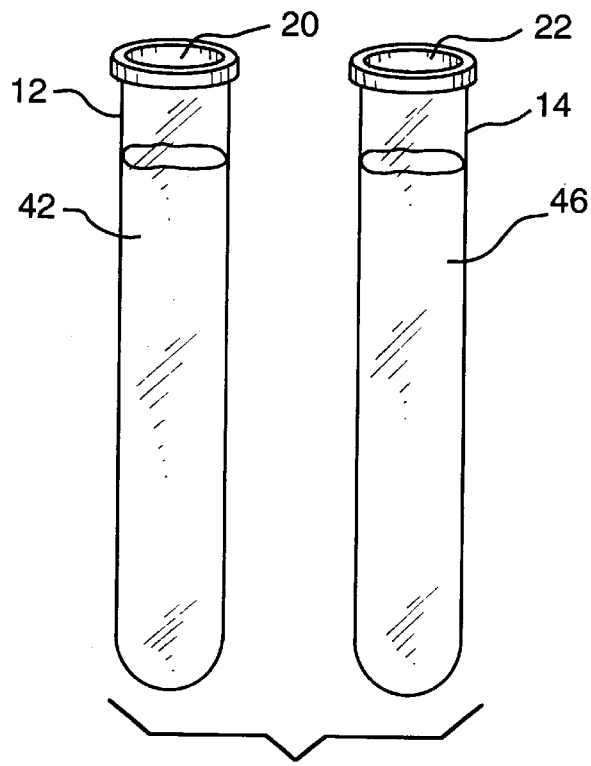
FIG. 2 is a perspective view of the two receptacles containing their respective aqueous broths.
Figure 3:
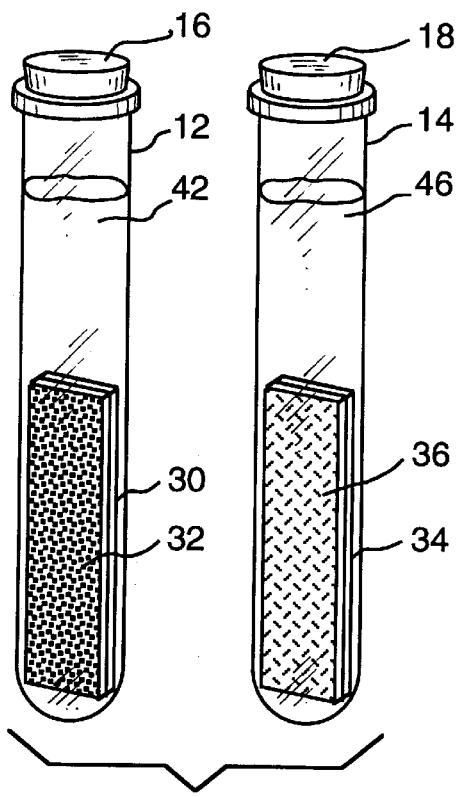
FIG. 3 is a perspective view similar to FIG. 2, only showing the respective slides and body specimens contained therein.
Figure 4:
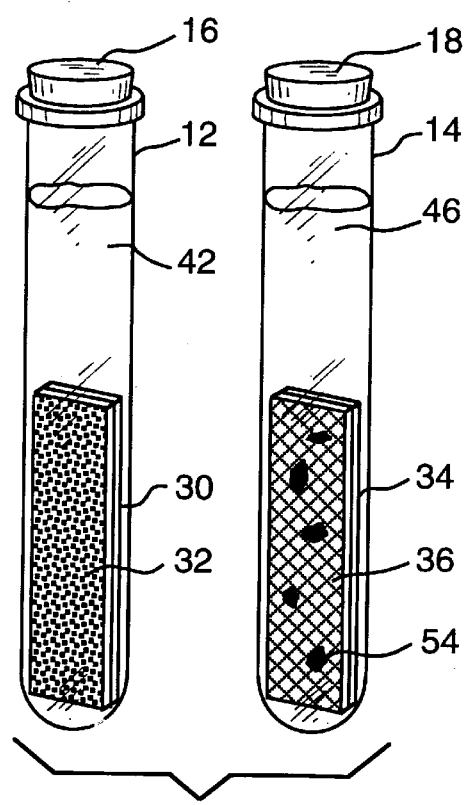
FIG. 4 is a perspective view similar to FIG. 3, only showing the lack of growth on the slide in the first receptacle and the presence of growth on the slide in the second receptacle.

With reference to FIGS. 2–4, the method of the invention will now be discussed. A body specimen is first taken from a patient. This body specimen can be sputum, fecal matter, cerebrospinal fluid, urine, gastric fluid, lymphatic material and purulent body fluids. The first test tube 12 and the second test tube 14 are taken from the kit 10 and are preferably placed side-by-side with the Czapek broth 42 being poured from the first container 40 into the first test tube 12 and the Middlebrook 7H9 broth 46 being poured from the second container 44 into the second test tube 14. After this, the first glass slide 30 having thereon the paraffin wax coating 32 and a portion of a body specimen are introduced into the Czapek broth 42 in the first test tube 12. The stopper 16 is then friction fit into the opening 20 of the first test tube. Similarly, the second glass slide 34 having thereon the hydrophobic material coating 36 and another portion of the body specimen are then introduced into the Middlebrook 7H9 broth 46 in the second test tube 14. The stopper 18 is then friction fit into the opening 22 of the second test tube 14.

If after several days (anywhere from 5–20 days), as shown in FIG. 4, there is (i) a lack of microorganism growth on the slide 30 coated with paraffin wax 32 and (ii) there is a presence of microorganism growth 54 on the second slide 34 coated with a hydrophobic material 36, it can be determined with a high rate of confidence that the body specimen contains a nonparaffinophilic hydrophobic microorganism, such as *M. tuberculosis*. This result can be further confirmed by doing an acid fastness assay (as is conventionally known and as is described in my U.S. Pat. No. 5,153,119, the disclosure of which is incorporated by reference herein). The result can also be further confirmed by using known gene probe technology (either with or without doing an acid fastness test).

The hydrophobic materials that can be used are paraffin wax or other waxes; plastics such as polypropylene, polyethylene, polystyrene, and tetrafluoroethylene; or silicones.

The invention utilizes the inventor's unexpected finding that *M. tuberculosis* and *M. paratuberculosis* and other microorganisms were able to grow on paraffin or other hydrophobic materials in a nutrient rich broth media, such as Middlebrook 7H9 broth. The waxy cell walls of these microorganisms, it is thought, favors attachment to a hydrophobic surface, such as paraffin wax, and thus the microorganism can imbibe the nutrients in the broth while being attached to the paraffin wax. In this way, paraffin baiting, as is described in my earlier U.S. Patents, can be combined with this so-called "hydrophobic baiting" to determine the presence or absence of these nonparaffinophilic hydrophobic microorganisms in a body specimen.

EXAMPLE

A patient comes into a doctor's office complaining of coughing, chronic fatigue, night sweats and loss of weight. The doctor suspects the patient has tuberculosis. The doctor obtains a sputum sample and introduces a portion of the sample into a first receptacle 12 containing the Czapek broth 42 only and a first slide 30 having a paraffin wax coating 32 and another portion of the sample into a second receptacle 14 containing the Middlebrook 7H9 broth 46 and a second slide 34 having a hydrophobic material coating, such as paraffin wax, 36. After several days, there is a lack of growth on the slide 30 having a paraffin wax coating 32 and there is positive growth on the slide 34 having a hydrophobic material coating 36. The doctor is fairly confident that the patient has *M. tuberculosis* and does an acid fastness assay test to confirm this conclusion.

It will be appreciated that a method and kit are provided to determine the presence or absence of a nonparaffinophilic hydrophobic microorganism in a body specimen are provided. The method is simple and efficient and the kit itself is fairly inexpensive.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of determining a presence or absence of a nonparaffinophilic hydrophobic microorganism in a body specimen comprising:

providing a first receptacle and a second receptacle, said first receptacle containing a sterile aqueous broth and said second receptacle containing an aqueous broth including a carbon source;

placing into said first receptacle a first support surface having a paraffin wax coating thereon;

placing into said second receptacle a second support surface having a hydrophobic material coating thereon;

introducing into each of said first and second receptacles said body specimen; and determining said presence of said nonparaffinophilic hydrophobic microorganism in said body specimen by observing (i) lack of microorganism growth on said paraffin coated material of said first support surface and (ii) a presence of microorganism growth on said hydrophobic material coating of said second support surface.

2. The method of claim 1, including further confirming said presence of said nonparaffinophilic hydrophobic microorganism in said body specimen by performing an acid fastness assay on said microorganism growth which is present on said hydrophobic material coating of said second support surface.

3. The method of claim 1, including said hydrophobic nonparaffinophilic is selected from the group consisting of *M. tuberculosis* complex, *M. paratuberculosis, M. leprae, pseudomonads,* and nocardial species.

4. The method of claim 1, wherein said first receptacle is a test tube; and said first support surface is a glass slide.

5. The method of claim 4, wherein said second receptacle is a test tube; and said second support surface is a glass slide.

6. The method of claim 1, wherein said hydrophobic coating material is selected from the group consisting of waxes, silicones and plastics.

7. The method of claim 6, wherein said plastics include polypropylene, polyethylene, polystyrene and tetrafluoroethylene.

8. The method of claim 1, wherein said body specimen is sputum, fecal matter, cerebrospinal fluid, urine, gastric fluid, lymphatic material and purulent body fluids.

9. A kit for determining a presence or absence of a nonparaffinophilic hydrophobic microorganism in a body specimen comprising:

a first receptacle;

a second receptacle;

a first support surface having a paraffin wax coating thereon; and a second support surface having a hydrophobic material coating thereon.

10. The kit of claim 9, including a first container having a sterile aqueous broth therein; and a second container having an aqueous broth including a carbon source.

11. The kit of claim 9, including an acid-fast assay means.

12. The kit of claim 9, wherein said first receptacle is a test tube; and said first support surface is a glass slide.

13. The kit of claim 12, wherein said second receptacle is a test tube; and said second support surface is a glass slide.

14. The kit of claim 9, wherein said hydrophobic coating material is selected from the group consisting of waxes, silicones and plastics.

15. The kit of claim 14, wherein said plastics include polypropylene, polyethylene, polystyrene and tetrafluoroethylene.

* * * * *